United States Patent
Doucas et al.

(12) 
(10) Patent No.: US 6,319,663 B1
(45) Date of Patent: *Nov. 20, 2001

(54) METHOD FOR THE IDENTIFICATION AND USE OF SUBSTANCES THAT MODULATE POD FUNCTION AND/OR STRUCTURE

(75) Inventors: Vassilis Doucas, Geneva (CH); Ronald M. Evans, La Jolla, CA (US)

(73) Assignee: The Salk Institute for Biological Studies, La Jolla, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/975,272

(22) Filed: Nov. 21, 1997

(51) Int. Cl.$^7$ ............................... C12Q 1/00; C12Q 1/68; C12N 5/10; C12N 15/12
(52) U.S. Cl. .................. 435/4; 435/5; 435/6; 435/69.1; 530/350; 536/23.5; 536/23.72
(58) Field of Search .............................. 435/4, 5, 6, 69.1; 530/350; 536/23.5, 23.72

(56) References Cited

PUBLICATIONS

Doucas et al. Human T–cell leukemia retrovirus–Tax protein is a repressor of nuclear receptor signaling. Proc. Natl. Acad. Sci. USA vol. 96 pp. 2633–2638, 1999.*
Desbois et al. Exclusion of Int–6 from PML nuclear bodies by binding to the HTLV–1 Tax oncoprotein. Science vol. 273 pp. 951–953, 1999.*
Orkin et al. Report and recommendations of the panel to assess the NIH investment on research on gene therapy. www.nih.gov/news/panelrep.html, 1995.*
Stadler et al. Transcriptional induction of the PML growth suppressor gene by interferons is mediated through an ISRE and a GAS element. Oncogene vol. 11, pp. 2565–2573, 1995.*
Andre, et al., "The PML and PML/PARα Domains: From Autoimmunity to Molecular Oncology and from Retinoic Acid to Arsinec[1]" *Experimental Cell Research* 229:253–260 (1996).
Avantaggiati, et al., "Recruitment of p300/CBP in p53–Dependent Signal Pathways" *Cell* 89:1175–1184 (1997).
Blondel, et al., "Efficient induction of focus formation in a subclone of NIH3T3 cells by c–myc and its inhibition by serum and by growth factors" *Oncogene* 5:857–865 (1990).
Brazas and Ganem, "A Cellular Homolog of Hepatitis Delta Antigen: Implications for Viral Replication and Evolution" *Science* 274:90–94 (1996).
Chiao, et al., "Autoregulation of IκBα activity" *Proc. Natl. Acad. Sci. USA* 91:28–32 (1994).
Doucas and Evans, "The PML nuclear compartment and cancer" *Biochimica et Biophysica Acta* 1288:M25–M29 (1996).

Doucas, et al., "Adenovirus replication is coupled with the dynamic properties of the PML nuclear structure" *Genes &Development* 10:196–207 (1996).
Doucas, et al., "The PML–retinoic acid receptor α translocation converts the receptor from an inhibitor to a retinoic acid–dependent activator of transcription factor AP–1" *Proc. Natl. Acad. Sci. USA* 90:9345–9349 (1993).
Evans, "The Steroid and Thyroid Hormone Receptor Superfamily" *Science* 240:889–895 (1988).
Gongora, et al., "Molecular Cloning of a New Interferon–induced PML Nuclear Body–associated Protein" *The Journal of Biological Chemistry* 272(31) 19457–19463 (1997).
Hollengerg and Evans, "Multiple and Cooperative Trans–Activation Domains of the Human Glucocorticoid Receptor" *Cell* 55:899–906 (1988).
Lowry, et al., "Protein Measurement with the Folin Phenol Reagent" *The Journal of Biological Chemistry* 193:265–274 (1951).
Miller and Whelan, "Progress in Transcriptionally Targeted and Regulatable Vectors for Genetic Therapy" *Human Gene Therapy* 8:803–815 (1997).
Naldini, et al., "In Vivo Gene Delivery and Stable Transduction of Nondividing Cells by a Lentiviral Vector" *Science* 272:263–267 (1996).
Ogryzko, et al., "The Transcriptional Coactivators p300 and CBP Are Histone Acetyltransferases" *Cell* 87:953–959 (1996).
Rottman, et al., "A Retinoic Acid–Responsive Element in the Apolipoprotein AI Gene Distinguishes between Two Different Retinoic Acid Response Pathways" *Molecular and Cellular Biology* 11(7) 3814–3820 (1991).
Tontonoz, et al., "Terminal differentiation of human liposarcoma cells induced by ligands for peroxisome proliferator–activated receptor γ and the retinoid X receptor" *Proc. Natl. Acad. Sci. USA* 94:237–241 (1997).
Tsai and O'Malley, "Molecular Mechanisms of Action of Steroid/Thyroid Receptor Superfamily Members" *Annu. Rev. Biochem.* 63:451–486 (1994).
Wahli and Martinez, "Superfamily of steroid nuclear receptors: positive and negative regulators of gene expression" *The FASEB Journal* 5:2243–2249 (1991).
Wet, et al, "Firefly Luciferase Gene: Structure and Expression in Mammalian Cells" *Molecular and Cellular Biology* 7(2) 725–737 (1987).
Wilson, J. M., "Vectors—shuttle vehicles for gene therapy" *Clin Exp Immunol* 107 (Suppl. 1):31–32 (1997).

* cited by examiner

*Primary Examiner*—John S. Brusca
(74) *Attorney, Agent, or Firm*—Stephen E. Reiter; Foley & Lardner

(57) ABSTRACT

The invention disclosed herein comprises assay methods for identifying substances useful for treating pathogenic disorders. The assay methods disclosed herein are based on the discovery that POD function and structure are key elements in normal transcriptional processes. Disruption of POD function and/or structure contributes to the creation and/or maintenance of a variety of pathogenic disorders.

25 Claims, No Drawings

METHOD FOR THE IDENTIFICATION AND USE OF SUBSTANCES THAT MODULATE POD FUNCTION AND/OR STRUCTURE

FIELD OF THE INVENTION

This invention relates to assay methods that can be used to identify substances valuable in the treatment of pathogenic disorders. In a particular aspect, the invention relates to assay methods for identification of substances useful for treatment of disorders related to transcription, translation and replication such as viral infections, cancer, inflammatory disorders and in particular disorders involving nuclear receptor functioning. In another aspect, the invention relates to methods for using substances, identified employing assay methods of the invention, for the treatment of pathogenic disorders. An additional aspect of the invention relates to methods for evaluating viral vectors for their usefulness in gene therapy.

BACKGROUND OF THE INVENTION

Some of the processes by which a cell utilizes its genetic material to direct its growth, differentiation, and other functions include transcription, translation, and replication. Transcription is the process by which DNA is converted into RNA for subsequent translation into a protein. Replication is the process by which DNA sequences are duplicated prior to cell division. These processes represent the principle activities localized in the cell nucleus.

Transcription is a complex process that controls gene expression and largely determines the actions and properties of cells. Most eukaryotic genes are regulated by multiple transcription-control elements, specific DNA sequences lying outside of the coding region of the gene. Transcription-control elements serve as specific binding sites for a variety of protein transcription factors, both activators and repressors.

In general, transcription activators are believed to control the assembly of the transcription initiation complex and the rate at which the poised RNA polymerase in this complex initiates transcription. The common feature among transcription activators is that each binds to one or several specific DNA regulatory elements, then participates in moderating the activity of the transcriptional apparatus. Generally transcriptional activators act in response to a cascade of intracellular reactions initiated by an extracellular signal. Although capable of acting alone, transcription activators are also known to interact with additional protein components, called coactivators, that can modify their activities. Well known transcription activators include the nuclear receptors, NF-κB, cAMP-response element binding protein (CREB), and the STATs.

The nuclear receptors, also known as steroid/retinoid hormone receptors, are transcription factors that exist in an inactive form either in the cytoplasm or nucleus. Upon binding their respective hormonal ligands, the receptors undergo activation or "transformation," and the activated receptor can then effectively bind to DNA and activate transcription of a cis-linked gene. Well known examples of nuclear receptors include the glucocorticoid receptor (GR), the retinoid receptors (RAR and RXR), the estrogen receptor (ER), the mineralocorticoid receptor (MR), the androgen receptor (AR), the progesterone receptor (PR), peroxisome proliferator-activated receptors (PPAR), vitamin D receptor (VDR), thyroid hormone receptor (THR) and the like. Reviews discussing the structure and function of nuclear receptors are found in Wahli and Martinez, FASEB J 5:2243–2249, 1991; Evans, Science 240:889–895, 1988; and Tsai and O'Malley, Annu. Rev. Biochem. 63;451–486, 1994, all of which are hereby incorporated by reference in their entirety. Nuclear receptor activity effects such diverse cellular functions as differentiation, proliferation and inflammatory response.

Nuclear factor-kappa B (NF-κB) encompasses a family of inducible transcriptional activators critical in the regulation of gene expression in the lymphocytic response to injury and inflammatory stimuli. In the cell, NF-κB exists as a homo- or heterodimer with distinct DNA binding specificities. Cellular stimulation with inflammatory cytokines, such as the interleukins, and other inflammatory stimuli results in the rapid translocation of NF-κB to the nucleus where it binds to specific κB elements. Many genes involved in the inflammatory response are induced by NF-κB including pro-inflammatory cytokines, chemotactic proteins and adhesion molecules. Steroids and retinoids are widely reported to exert anti-proliferative and anti-inflammatory effects in T lymphocytes in part by repressing the activities of NF-κB (and AP-1). In turn, NF-κB activity represses nuclear receptor function.

Elevation in the level of cytosolic cAMP, such as in response to G-coupled protein receptor activity, induces the expression of many genes. These genes are under the control of a cAMP-response element (CRE), essential for their induction, which is bound by the transcription activator CREB (cAMP-response element binding protein). CREB activity is promoted by its phosphorylation, which recruits the coactivator CREB-binding protein (CBP/p300). CBP can act as a coactivator for a number of other transcription activators including c-Jun, c-Myb, c-Fos, NF-κB and nuclear receptors, among others. CBP/p300 interacts with the transcription factor and tumor suppressor p53 and modulates its activity (Avantaggiati, et al Cell 89:1175–1184, 1997). In addition to its activity as a transcription factor, CBP enzymatically acetylates histones and other proteins, such as p53. This acetylation activity promotes CBP-dependent regulation of chromatin functioning, (Ogryzko, et al. Cell 87:953–959, 1996). Thus, CBP may perform an important role in the integration of diverse signaling pathways that result in changes in gene expression.

The cytokine-receptor superfamily includes receptors for protein ligands such as the interferons, erthryropoetin, and the like. Transcriptional activation in response to these receptors involves the phosphorylation and subsequent dimerization of a family of transcriptional activators called the STATs (Signal Transducers and Activators of Transcription). STATs can form homo- or heterodimers and bind to a number of DNA sequences including the interferon-stimulated response-element (ISRE) and the serum-inducible response element (SRE). STAT activity can also be induced by the activity of some tyrosine kinase receptors, such as the epidermal growth factor receptor. STAT activity regulates the expression of therapeutically important genes. In response to the binding of interferon, for example, cells are induced to express a set of proteins that make them resistant to viral infection.

Recent research has uncovered new evidence for the localization of several nuclear activities in substructures that may contribute a topological function to these processes. The nuclei of cells contain a variety of substructures among which are several morphologically distinct types, called nuclear bodies, including sphere organelles and coiled bodies. A third type of nuclear body having a distinct nuclear topology has recently been described, and is variously referred to as the PML Oncogenic Domain (POD), Nuclear Domain (ND) 10, or Kr body. PODs and POD-localized proteins have been proposed as playing a role in transcription and may be involved in translation, replication and nuclear transport as well. PODs have been found in all the cell types examined to date, suggesting that they are a fundamental structure common to all cells.

PODs are comprised of a number of cellular proteins, all of unknown function, arranged in a vesicle-like structure around an electron dense core. Among these proteins are PML, Sp-100, PIF13, PIF31, ND52, ND55, and Isg20 (Doucas and Evans, Biochimica et Biophysica Acta 1288:M25–M29, 1996; Gongora, et al, J Biol Chem 272 (31):19457–19463, 1997). Several of these proteins (e.g., PML, Sp-100) are the targets of antibodies present in the serum of patients with autoimmune disorders such as primary bilary cirosis and systemic lupus erythramatosis (Andre, et al, Exp Cell Res 229:253–260, 1996).

A chief component of PODs is the protein PML. PML was originally identified by its role in Acute Promyelocytic Leukemia (APL), a disorder characterized by a chromosomal translocation (15;17) which fuses PML to the retinoic acid receptor resulting in a PML:RAR fusion product that retains most of the functional domains of its parental proteins.

PML contains several different protein:protein interaction domains including a cysteine-rich domain containing a RING finger motif and a coiled-coil or alpha-helical region. The presence of protein:protein interaction domains predicts that PML possesses a self-polymerizing feature that permits efficient packaging and transfer of bound target molecules into a round vesicle-like structure. In fact, PML:RAR forms homodimers and PML:RAR-PML heterodimers in vitro, which results in disruption of normal POD structure and may contribute to the oncogenic state in APL patients. Treatment with retenoic acid results both in restoration of POD structure and cellular differentiation with subsequent clinical remission.

POD structure has also been linked with viral replication. Doucas, et al have shown that infection with adenovirus disrupts POD structure (Doucas, et al, Genes & Dev. 10:196–207, 1996), as is also the case when cells are genetically engineered to express certain adenovirus proteins. POD disruption can be reduced, however, by an increase in the expression of PML, which also reduces viral replication. These results suggest that adenovirus replication may utilize POD components. It has not been demonstrated, however, that POD-associated proteins directly contribute to transcriptional/translational/replication control nor has a role for PODs been shown using clinically relevant viruses.

A variety of serious pathogenic disorders involve transcription and translation at some level. For example, the process of inflammation requires the transcription and translation of a variety of proteins such as inflammatory cytokines and chemokines, and the like. Current anti-inflammatory treatments strive to ameliorate the undesirable effects of these proteins with varying degrees of success, often producing severe side effects. A substance capable of regulating the transcription and/or translation of inflammatory proteins could modulate the inflammatory process without the side effects of current treatments.

Cancer is another pathogenic disorder that involves transcriptional and translational regulation. Disruption of normal transcription can result in an inability of cells to differentiate, for example, a hallmark of the cancerous state. Restoration of transcription would allow these cancer cells to resume a normal differentiation pathway, ultimately ending in apoptosis. To date, however, many, if not most treatments for cancer involve the use of cytotoxic agents which target and kill any rapidly dividing cell, including those that are perfectly normal. Therefore, a need still exists for new methods of treating cancer that are more selective and have fewer side effects.

Viral infections, such as with the human immunodeficiency virus, can have a severe debilitating effect on the infected host. Viruses themselves are simple organisms lacking the full range of transcriptional machinery necessary for their efficient propagation in the cell. Most viruses rely on their ability to co-opt the transcriptional/translational apparatus of their hosts in order to multiply. The anti-viral therapies currently in use often target viral specific proteins, such as viral proteases. The rapid replication and mutation rate of most viruses, however, often allows new strains to emerge that are resistant to these therapies.

Thus a need exists for new substances that can be used to treat these and other pathogenic disorders. The invention disclosed herein addresses that need.

BRIEF DESCRIPTION OF THE INVENTION

The invention disclosed herein comprises assay methods for identifying substances useful for treating pathogenic disorders. The assay methods disclosed herein are based on the discovery that POD function and structure are key elements in the coordination of regulatory signals needed for normal transcription, translation, replication, nuclear import/export and RNA processing. Disruption of POD function and/or structure contributes to the creation and/or maintenance of a variety of pathogenic disorders.

In accordance with another aspect of the present invention, it has further been discovered that restoration of POD function and/or structure has a beneficial treatment effect and can contribute to restoration of normal function in the organism so effected.

In accordance with another aspect of the invention there is provided a method for designing viral vectors useful for gene therapy. Many methods of delivering exogenous genetic material to cells for therapeutic purposes involve the use of viral vectors. The discovery that certain viral proteins significantly disrupt normal cellular transcription and translation suggests that gene therapy delivery vehicles based on viral vectors should avoid the presence of these viral proteins in order to avoid the potential for deleterious effects on normal cellular function.

Thus the present invention provides methods for identifying useful therapeutic substances, including those useful in treating viral and inflammatory disorders and in gene therapy, and methods for their use.

DETAILED DESCRIPTION OF THE INVENTION

The invention disclosed herein comprises assay methods for identifying substances useful for treating pathogenic disorders. Invention methods comprise: a) contacting a test cell with a test substance and b) assaying for the ability of the substance to modulate POD function and/or structure. By "modulate" it is meant that the substance can either inhibit, enhance or restore POD function and/or structure.

In one aspect of the present invention, a test substance can be identified as a potentially useful therapeutic agent by its ability to enhance or restore POD function and/or structure by increasing levels of a POD-localized protein. The inventors have discovered that an increase in the levels of POD-localized proteins has a beneficial therapeutic effect on cells infected with viruses that cause serious disease in humans, such as the human T-lymphotropic virus (HTLV-1) which is associated with adult T-cell leukemia (ATLL) and inflammatory neurological diseases such as tropical spastic paraparesis (TSP). As seen in the Examples below, increasing the expression of the POD-localized protein PML reverses the pathogenic effects of the HTLV-1 protein Tax.

Of particular interest is the relationship between POD function and structure and viruses such as HTLVs 1 and 2 and HIV. This group of viruses is unique in that their genome consists of a single strand of RNA which encodes, among other things, a reverse transcriptase enzyme which transcribes the viral RNA into DNA in the host cell. This is in contrast to viruses whose genomic material is DNA which can be readily integrated in to the host genome. The profound effects of the Tax protein of HTLV-1 on POD function and structure are triking in light of the distinctive nature of these types of viruses.

Increase in POD-localized protein levels can be identified by measuring for upregulation of mRNA encoding a POD-localized protein, or of the promoter of a POD-localized protein or by direct measurement of the protein itself. By "POD-localized protein" it is meant a protein naturally occurring in a cell, said protein further being naturally localized to a POD structure, either permanently or in response to some cellular signal. Examples of POD-localized proteins include PML, Sp-100, CBP, PIF13, PIF31, ND52, ND55, Isp20, DipA, and the like.

A variety of methods are known to those skilled in the art that can be employed to measure upregulation of mRNA, proteins or promoter activity. Levels of mRNA, for example, can be measured by isolating total RNA from treated test cells, transferring it to a solid support, such as a nylon membrane, and quantitating the mRNA so bound using a labeled complementary probe specific for mRNA encoding a POD-localized protein. Alternatively, after isolation, the RNA can be subjected to quantitative polymerase chain reaction (PCR) analysis using a POD-localized protein specific primer.

Upregulation of POD-localized protein promoter activity is likewise measurable by techniques known to those skilled in the art. For example, test cells can be transfected with a genetically engineered plasmid encoding a POD-localized protein promoter operably linked to a detectable gene product prior to incubation with a test substance. Increase in the quantity of detectable gene product would indicate upregulation of POD-localized protein promoter activity. This method is illustrated in the Examples below using the PML promoter and a gene encoding luciferase as the detectable gene product.

Alternatively, one may directly measure levels of a POD-localized protein to determine if its synthesis has been upregulated. Detection methods include the use of POD-localized protein-specific antibodies (monoclonal or polyclonal) in in situ hybridization or immunoprecipitation. The POD-localized protein-specific antibodies can be themselves conjugated to a detectable label, such as a fluorescent label or enzymatic label, and the like. Additionally, the POD-localized protein-specific antibodies can be unlabeled and detected with a secondary antibody, such as an anti-IgG, anti-IgM, and the like, that is labeled with a detectable label.

An increase in POD-localized protein levels can also be measured by isolation of the protein from test cells using protein fractionation methods, such as column chromatography, gel filtration, and the like, and subsequent determination of the amount of protein so obtained, such as by using the method of Lowry, et al (Lowry, et al, J Biol Chem 193:265, 1951). Methods for protein isolation and quantitative estimation are well known to those skilled in the art.

In another aspect of the invention, an additional assay step can be included, i.e. causing the test cell to express one or more viral proteins prior to assaying for the ability of the test substance to modulate POD function and/or structure. Test cells can, for example, simply be infected with a virus using methods well known to those skilled in the art. Alternatively, test cells can be genetically engineered to express selected viral proteins. In some cases, such as with Tax, the viral protein can simply be added to the media in which the test cells are grown. Any virus of interest can be used, however particularly preferred viruses include adenovirus, herpes viruses, human immunodeficiency virus (HIV), HTLV viruses 1 and 2, hepatitis viruses, papilloma virus, varicella virus, and the like. Particularly preferred viral proteins for genetically engineered expression include E4-ORF3 and E4-ORF6 of adenovirus, Tax from HTLV-1, and the like.

The methods described above for assessing the activity of a test substance can be used in assays comprising this additional step. Alternatively, the activity of test substances can be evaluated by their ability to 1) modulate the disruption of POD morphology, or 2) modulate the degradation of POD-localized proteins.

The ability of a test substance to maintain or restore normal POD morphology would be an indication of potential therapeutic activity. PODs are normally found in the nucleus arranged in a punctate-type structure. In several disorders, such as cancer or viral infection, however, the punctate morphology is often disrupted. This disruption can be detected using in situ hybridization techniques with a POD-localized protein-specific antibody (polyclonal or monoclonal) labeled with a detectable label as described above.

Additional methods of assessing the potential of a test substance to act as an anti-viral agent is by its ability to disrupt viral-protein:POD-localized-protein interactions or by its ability to prevent virus-induced POD-localized protein degradation/disassociation. Both can be evaluated using, for example, labeled antibodies, in the former case one specific for the viral protein and one specific for the POD-localized protein, and the techniques discussed above.

The inventors have shown that PODs and POD-localized proteins play an important role in the function of nuclear receptors. Thus, in yet another aspect of the invention, the therapeutic potential of a test substance is evaluated by its ability to modulate nuclear receptor-mediated transcription in cells expressing one or more viral proteins. This method comprises the steps of the assays disclosed above and includes the additional steps of 1) genetically engineering the test cell to express a nuclear receptor and reporter gene (described in more detail below) and 2) contacting the genetically engineered test cell with an agent known to activate the nuclear receptor. This assay method is disclosed in more detail in Example 6 below. A particularly useful viral protein employed for expression in a test cell in this aspect of the invention is the HTLV-1 Tax protein.

It is known that the oncoprotein Tax, a key protein in the replication of HTLV-1 and HIV-1, activates the transcriptional coactivator NF-κB. It is also known that NF-κB inhibits nuclear receptor function. In accordance with the present invention, it has been discovered that Tax expression also inhibits nuclear receptor function, showing a synergistic effect with NF-κB, and additionally disrupts normal POD morphology. These effects can be overcome by increased expression of a POD-localized protein, for example PML. Furthermore, in accordance with the present invention, it has been discovered that the transcription factor CBP, an essential coactivator of nuclear receptor activity, localizes to the POD through its binding to the POD-localized protein PML. This work strongly suggests that a modulator of POD function and/or structure would have a beneficial effect in treating disorders dependent on nuclear receptor function.

Suitable nuclear receptors useful in this aspect of the invention include the glucocorticoid receptor (GR), the retinoid receptors (RXRs, RARS), prostaglandin receptors (PPARs), and the like. Suitable reporter genes include luciferase, chloramphenicol acetyl transferase, and the like, under the control of the various promoters such as MMTV (mouse mammary tumor virus), apolipoprotein A1 (Apol4-tk), AP2 promoter, thymidine kinase promoter, collagenase promoter, synthetic promoters containing regulatory elements, such as DR1-5 and the β-response element, synthetic promoters containing regulatory elements for PPARα, β, and γ, natural promoters regulated by nuclear receptors, and the like.

In test cells expressing a nuclear receptor, a reporter construct and Tax, a test substance showing therapeutic potential will show increased transcriptional activity when treated with a stimulator of nuclear receptor activity (such as dexamethasone) compared to test cells not exposed to the test substance. Since it has also been discovered, in accordance with the invention, that Tax synergizes with NF-κB, this assay may be slightly modified such that the test cells are additionally genetically engineered to express NF-κB.

Test cells suitable for use in the assays of the invention include mammalian cells, insect cells, fungal cells, bacterial cells, and the like. Preferred test cells are mammalian cells, particularly those that have been adapted to cell culture (more commonly called cell lines). Particularly preferred test cells include CV-1 (ATCC CCL 70), Hep-2 (ATCC CCL 23), NB-4 (Duprez, et al, Leukemia 6:1281–1287, 1992), NIH3T3 L1 cells (Blondel, et al, Oncogene 5:857–865, 1990), P4-2 cells (Naldini, et al, Science 272:263–267, 1996) liposarcoma cell lines LS857, LS175, LS707 (Tontonoz, et al. PNAS 94:237–241, 1997) and the like.

Test cells can be grown under in vitro cell culture conditions using techniques well known in the art. Alternatively the test cells can be grown in vivo as part of an animal. Common sources of suitable test cells include, for example, the American Type Culture Collection, Bethesda, Md. (ATCC).

Suitable test substances for use in the assays of the invention include proteins, peptides, lipids, carbohydrates, extracts from fungal or plant sources, small organic molecules, and the like. Sources of these test substances include conditioned cell culture media, commercially available libraries of compounds (small organic molecules, peptides), and the like.

In another aspect of the invention, substances are identified that inhibit nuclear receptor function. Such substances are useful, for example, in treating disorders such as diabetes or obesity where a reduction in mature adipocytes is desired. The inventors have discovered that Tax expression inhibits the nuclear receptor driven differentiation of adipocytes. Substances mimicking Tax activity could, therefore, be useful as therapeutics. Test cells as described above are genetically engineered to express a nuclear receptor and a reporter gene contruct. Test substances are then assessed for their ability to inhibit nuclear receptor activity such as disrupting POD structure and/or function.

Also encompassed in the present application is a method of treating pathogenic disorders with a substance capable of modulating POD structure and/or function. Treatment methods in accordance with the invention comprise administering the substance in an amount sufficient to modulate POD structure and/or function. The organism to be so treated is preferably a mammal, and most preferably human.

The particular substance selected for use in treatment can be administered to a patient either by itself or in a pharmaceutical composition where it is mixed with suitable carriers or excipient(s). In treating a patient, a therapeutically effective dose of the substance is administered. A therapeutically effective dose refers to that amount of the substance that results in amelioration of symptoms or a prolongation of survival in a patient.

Toxicity and therapeutic efficacy of such substances can be determined by standard pharmaceutical procedures in cell culture or experimental animals. Cell culture assays and animal studies can be used for determining the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. Substances which exhibit large therapeutic indices are preferred. The data obtained from these cell culture assays and animal studies can be used in formulating a range of dosages for use in humans. The dosage of such substances lies preferably within a range of circulating concentrations that include the $ED_{50}$ with little or no toxicity. The dosage may vary within this range depending upon a variety of factors, e.g., the dosage form employed, the route of administration utilized, the condition of the subject, and the like.

For any substance used in the method of the invention, the therapeutically effective dose can be estimated initially from cell culture assays by determining an $IC_{50}$ (i.e., the concentration of the test substance which achieves a half-maximal modulation of POD structure and/or function). A dose can then be formulated in animal models to achieve a circulating plasma concentration range that includes the $IC_{50}$ as determined in cell culture. Such information can be used to more accurately determine useful doses in humans. Levels in plasma may be measured, for example, by HPLC. The exact formulation, route of administration and dosage can be chosen by the individual physician in view of the patient's condition. (See e.g. Fingl et al., 1975, in "The Pharmacological Basis of Therapeutics", Ch. 1 pl ).

It should be noted that the attending physician would know how to and when to terminate, interrupt, or adjust administration due to toxicity, to organ dysfunctions, and the like. Conversely, the attending physician would also know to adjust treatment to higher levels if the clinical response were not adequate (precluding toxicity). The magnitude of an administered dose in the management of the oncogenic disorder of interest will vary with the severity of the condition to be treated, with the route of administration, and the like. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. Techniques for formulation and administration may be found in "Remington's Pharmaceutical Sciences," 1990, 18th ed., Mack Publishing Co., Easton, Pa. Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, the substances of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art.

Use of pharmaceutically acceptable carriers to formulate the substances herein disclosed for the practice of the invention into dosages suitable for systemic administration is within the scope of the invention. With proper choice of carrier and suitable manufacturing practice, the compositions of the present invention, in particular those formulated as solutions, may be administered parenterally, such as by intravenous injection. The substances can be formulated readily using pharmaceutically acceptable carriers well known in the art into dosages suitable for oral administration. Such carriers enable the substances of the invention to be formulated as tablets, pills, capsules, dragees, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Small organic molecules may be directly administered intracellularly due to their hydrophobicity.

Pharmaceutical compositions suitable for use in the present invention include compositions wherein the active ingredients are contained in an amount effective to achieve its intended purpose. Determination of an effective amount is well within the capability of those skilled in the art, especially in light of the detailed disclosure provided herein.

In addition to the active ingredients, these pharmaceutical compositions may contain suitable pharmaceutically acceptable excipients and auxiliaries which facilitate processing of the active compounds into preparations which can be used pharmaceutically.

The pharmaceutical compositions of the present invention may be manufactured in a manner that is itself known, e.g., by means of conventional mixing, dissolving, granulating, dragee-making, levigating, emulsifying, encapsulating, entrapping, lyophilizing processes, or the like.

Pharmaceutical formulations for parenteral administration include aqueous solutions of the active compounds in water-soluble form. Additionally, suspensions of the active substances may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions.

Pharmaceutical preparations for oral use can be obtained by combining the active substances with solid excipient, optionally grinding the resulting mixture, and processing the mixture of granules, after adding suitable auxiliaries, if desired, to obtain tablets or dragee cores.

Suitable excipients are, in particular, fillers such as sugars, including lactose, sucrose, mannitol, sorbitol, and the like; cellulose preparations such as, for example, maize starch, wheat starch, rice starch, potato starch, gelatin, gum tragacanth, methyl cellulose, hydroxypropylmethylcellulose, sodium carboxymethylcellulose, polyvinylpyrrolidone (PVP), and the like, as well as mixtures of any two or more thereof. If desired, disintegrating agents may be added, such as cross-linked polyvinyl pyrrolidone, agar, alginic acid or a salt thereof such as sodium alginate, and the like.

Dragee cores are provided with suitable coatings. For this purpose, concentrated sugar solutions may be used, which may optionally contain gum arabic, talc, polyvinyl pyrrolidone, carbopol gel, polyethylene glycol, titanium dioxide, lacquer solutions, suitable organic solvents or solvent mixtures, and the like. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Gene therapy has the potential to treat a variety of inherited and acquired disorders. The basic premise behind gene therapy is the introduction of exogenous genetic material into the cells of the organism to be treated. This has been most often accomplished using gene delivery vehicles, or vectors, based on recombinant versions of viruses, with retroviruses serving as prototypes (Wilson, Clin Exp Immunol 107(Suppl 1):31–32, 1997; Miller and Whelan, Hum Gene Ther 8(7):803–815, 1997).

In accordance with the present invention, the identification of the viral proteins that interfere with POD organization provides important information in the design of viral vectors. The techniques described above can be used to determine if the introduction of a viral vector proposed for use in gene therapy disrupts POD structure and/or function in such a way that the therapeutic gene being introduced into the cells is rejected.

The invention will now be described in greater detail by reference to the following non-limiting Examples.

EXAMPLES

Example 1
Assay for Identifying Therapeutic Substances by an Increase in POD-localized Proteins The following example describes assays for the identification of substances with the potential to be useful therapeutics. The assays measure an increase in POD-localized proteins in a test cell following contact with a test substance.

Test cells, such as Hep-2 cells, are placed in approximately equal numbers in wells of a 96 well microtiter plate and grown in standard growth media, such as, for example, Dulbecco's Modified Growth Media (DMEM)(Gibco) plus 5% fetal calf serum. Test substance is dissolved in a convenient solvent, water, phosphate buffered saline (PBS) or dimethylsulfoxide (DMSO) for example, and added to the wells containing the test cells. At various time points post-treatment, for example 0, 2, 6, and 12 hours post-treatment, the cell culture media is removed, and RNA isolated from the treated test cells using standard techniques. Quantitative reverse transcriptase-polymerase chain reaction assays are performed using the isolated RNA and employing appropriate primers obtained from cDNA encoding a POD-localized protein (such as PML or Sp-100). The amount of POD-localized protein specific RNA in test substance treated cells is compared to cells not exposed to a test substance. An increase in POD-localized protein specific RNA indicates that the test substance has the potential to be a useful therapeutic agent.

In a variation on this assay, isolated RNA is transferred to a solid support such as a nylon membrane, and the amount of POD-localized protein specific RNA detected using a specific nucleotide sequence that is capable of hybridizing to the POD-localized protein specific RNA.

Potential therapeutic agents are also identified by measuring amounts of POD-localized protein in treated cells. Test cells, such as Hep-2 cells, are place in approximately equal numbers in wells of a 96 well microtiter plate and grown in standard growth media. Test substance dissolved in a convenient solvent, water, phosphate buffered saline (PBS) or dimethylsulfoxide (DMSO) for example, and added to the wells containing the test cells. At various time points post-treatment, for example 0, 2, 6, and 12 hours post-treatment, the cell culture media is removed, and the cells fixed with freshly prepared paraformaldehyde in PBS at room temperature. The fixed cells are washed in PBS and permeabilized for 20 minutes on ice with 0.2% Triton X-100 in PBS (v/v). Alternatively, cells can be fixes at −20° C. for 5 minutes on ice with fresh, cold acetone, followed by fresh, cold absolute methanol.

The fixed cells are incubated with POD-localized protein-specific antibody conjugated to a detectable label, such as a fluorescent chromophore , under conditions that allow the antibody to bind to the POD-localized protein, generally about 1 hour at room temperature. The cells are washed to remove unbound antibody and the amount of antibody bound determined using the detectable label. The amount of POD-localized protein present in cells treated with a test substance is compared to untreated cells. An increase in POD-localized protein levels indicates that the test substance may be a useful therapeutic.

Alternatively, the assay procedure can be performed as above, however, rather that determining the amount of antibody bound quantitatively, the cells are visualized and evaluated for changes in POD morphology. Enlargement of the POD structure, for example, is an indication of an increase in POD-localized protein.

Example 2
Assay for Identifying Therapeutic Substances by Inhibiting Viral Effects on PODs The following example describes assays for the identification of potential therapeutic substances by measuring the ability of the substance to inhibit the negative effects of viral proteins on POD structure and/or function.

Test cells, such as Hep-2 or CV-1 cells, are placed in approximately equal numbers in wells of a 96 well microtiter plate and grown in standard growth media, such as, for example, DMEM (Gibco) plus 5% fetal calf serum. Test substance is dissolved in a convenient solvent, water, phosphate buffered saline (PBS) or dimethylsulfoxide (DMSO) for example, added to the wells containing the test cells and allowed to incubate for approximately 16 hours. The test cells are then transfected with an expression vector expressing a viral protein, such as E4-ORF3 from adenovirus, using standard transfection procedures (Doucas, et al, Genes & Dev, Supra). The test cells are provided with fresh growth medium and allowed to grow for approximately 24 hours. The cells are then fixed and treated with antibodies specific for a POD-localized protein, such as PML, and the viral protein using the procedures described in Example 1. Substances with therapeutic potential will block the ability of the viral protein to disorganize or degrade the POD-localized protein, which can be detected visually.

Example 3
The Effects of Tax Expression are Overcome by PML

The following example demonstrates that expression of HTLV-1 Tax protein disrupts POD structure and function and that this effect can be overcome by an increase in POD-localized protein expression.

Hep-2 cells were transfected with pcTax1 expression vector (expressing HTLV-1 Tax protein) and fixed 48 hours later as described in Doucas, et al, Genes Dev. 10:196–207, 1996. Antigen localization was determined with double incubation of fixed cells with Tax specific antibodies (Ab6605 (rabbit), Ab1189 (goat)) and the PML-specific monoclonal antibody followed by incubation with a secondary monoclonal antibody conjugated to fluorescein or Texas red as previously described in Doucas, et al, supra. Fluorescence images were analyzed using a Nikon Microshoft-SA immunofluorescence microscope.

POD structure was significantly disrupted in cells expressing Tax protein. Anti-PML antibody showed that PML had been removed from its normal nuclear location and redistributed to co-localize with Tax either perinuclearly or in the cytoplasm. In the majority of experiments, the PML was partially distributed in track-like structures.

A similar experiment was conducted to determine if an increase in POD-localized protein expression could reverse the disruptive effects of Tax. CV-1 cells were co-transfected with pcTax1 and CMXHA-PML (a vector expressing PML, Doucas, et al, supra). The cells were fixed 36–48 hours later and Tax and PML proteins visualized with antibodies as described above. Increase in PML expression reversed the Tax-induced disruption of the POD structure and returned PML localization to the nucleus.

Example 4
Human Immunodefficiency Virus Localizes to PODs

The following example demonstrates that the human Immunodeficiency virus localizes to the PODs after infection, much as does HTLV-1. Furthermore, POD proteins appear to facilite transfer of HIV RNA to the nucleus after infection. Substances that restore POD structure and/or function would be useful, therefore, in treating HIV infection.

P4-2 cells (Naldini, et al, Science 272:263–267, 1996) were grown in round coverslips and maintained in DMEM supplemented with 10% fetal calf serum in a humidified atmosphere containing 5% $CO_2$. The cells were infected with two different concentrations (100 ng and 1 μg) of HIV virus, (HIV-1 (W13) wt.) or no virus (empty). Cells were fixed at 3, 6, 9, 24, 32, hrs post-infection by incubating at room temperature for 5 min. with freshly prepared 1% paraformaldehyde in PBS, washed with PBS, and permeabilized for 20 min on ice with 0.2% Triton X-100 in PBS (v/v) (Sigma Chemical Co.).

For the detection of HIV-RNA in the infected cells, fixed coverslips were incubated for 10 hrs at 42° C. with 50 ng of a HIV-1-specific 300 bp RNA probe labeled with fluorescent UTP, in a solution containing 50% formamide. Cells were washed in a PBS/SDS/NaCL solution for 90 min. To detect PML, the washed cells were incubated with anti-PML antibodies. Cells were incubated with the first Ab diluted in PBS-10% calf serum for two hrs at RT in a humidified chamber. Coverslips were washed for 10 min in PBS—0.05% Tween 20. The conjugated to Texas red second monoclonal Ab (Jackson Lab.) was applied for 1 hr at RT in the humidified chamber. Cells were analyzed in a light or confocal microscopy.

In cells infected with HIV, virus was detected in the nucleus co-localized with PML. POD structure was additionally reorganized with PML being detectable perinuclearly or in the cytoplasm. Furthermore, the localization of PML and HIV over time suggests that PML is moving into the cytoplasm and facilitating import of HIVRNA into the nucleus.

Example 5
DipA is a POD-localized Protein

The following example demonstrates that DipA is a POD-localized protein. DipA is a mammalian counterpart to a protein encoded by the hepatitis delta virus (HDV) (Brazas and Ganem, Science 274:90–94, 1996). Previous research suggested that DipA might be involved in HDV replication, although the mechanism was unknown (Brazas, supra). The inventors have discovered that DipA is a POD-localized protein, thus linking POD structure and function to control of HDV replication.

Hep-2 cells were grown in round coverslips and maintained in DMEM supplemented with 10% fetal calf serum in a humidified atmosphere containing 5% $CO_2$. Cells were treated with 5 μg of gamma interferon (Biosource) or mocked treated for 18 hrs before fixation. Cells were fixed by one of two methods. In a first method, the cells were fixed at room temperature for 5 min with freshly prepared 1% paraformaldehyde in PBS, washed with PBS, and permeabilized for 20 min on ice with 0.2% Triton X-100 in PBS (v/v) (Sigma Chemical Co.). Antigen localization (PML and DipA) was determined after incubation of permeabilized cells with rabbit antiserum (DipA Ab) and a specific PML mAb diluted in PBS for 1 hr at RT. Cells were double labeled with the respective second antibodies labeled either with FITC or Texas red, using FITC for the structures with the lowest staining intensity.

Alternatively, cells were fixed at −20° C. for 5 min with fresh and cold acetone followed by fresh and cold absolute methanol.

The cells were incubated with the first Ab diluted in PBS-10% calf serum for two hrs at RT in a humidified chamber. Coverslips were washed for 10 min in PBS—0.05% Tween 20. The conjugated to fluorescein or Texas red second monoclonal Abs (Jackson Lab.) were applied for 1 hr at RT in the humidified chamber. For double immunofluorescence, permeabilized cells were incubated with the two Abs under the same conditions. Cells were then stained for DNA with 0.5 μg/ml of bis-benzimide (Hoecht 33258; Sigma) in PBS or with 0.5 μg/ml DAPI and mounted with gelvatol or Fluoromount G (Fischer Scientific). The two fixation methods gave similar results.

Fluorescence images were analyzed using either the Leica confocal scanning microscope or a Nikon Microphot-SA immunofluorescence microscope. Confocal images represent single optical sections obtained either by simultaneous or sequential scanning.

In these experiments, DipA protein localized in the POD structure. It is of interest to note the increased co-localization of PML and DipA in the POD structures in interferon gamma treated cells, and the exclusive localization of DipA in specific structures in the nucleoli.

Example 6
Tax-mediated Inhibition of Nuclear Receptor Function is Reversed by an Increase in PML Expression The following example demonstrates that Tax synergizes with NF-κB to inhibit nuclear receptor function and that this inhibition can be reverse by an increase in PML. These results suggest that substances that increase POD-localized proteins and/or restore POD function will be useful as anti-inflammatory treatments and in treating other disorders involving nuclear receptor function.

a) Tax expression activates NF-κB and inhibits nuclear receptor function

CV-1 cells were transfected with expression plasmids expressing either Tax (pcTax), NF-κB (CMXp65) or both as described in Doucas and Evans, supra in addition to a reporter gene, Igκ-tk-Luc. The Igκ-tk-Luc reporter contains six oligonucleotides corresponding to the κB-site of the immunoglobulin κ-light chain enhancer (Chiao, et al, Proc Natl Acad Sci USA 91:28–32, 1994) linked to the minimal thymidine kinase promoter upstream of the coding sequence for the luciferase gene (de Wet, et al, Mol Cell Biol 7:725–737, 1987). The CMXp65 and pcTax expression vectors were transfected at 0.12 μg and 0.18 μg, respectively. Transient expression of Tax or NF-κB stimulated the transcription of an Igκ-tk-Luc reporter gene by 6 and 12 fold, respectively.

A similar experiment was done to asses the effect of Tax expression on nuclear receptor activity. Transient expression of the glucocorticoid receptor (GR) in CV-1 cells activates the transcription of the MMTV-Luc reporter by 450-fold in the presence of 1 μM dexamethasone (Doucas, Genes & Dev, supra). For this experiment, 0.10 μg of MMTV-Luc, 0.075 μg of GR and 0.15 μg of pcTaxI and pcTaxII expression vectors were trasfected per 30,000–40,000 cells together with 0.075 μg of a beta-galactosidase expression vector as an internal control. Co-transfect of either TaxI or TaxII repressed GR activity to a level of less than 100 units.

CV-1 cells were transfected with MMTV-Luc reporter gene, GR and 0.075 μg of CMXp65 in a similar experiment. Transient expression of p65 (NF-κB) repressed the activity of GR 8-fold. Co-transfection of Tax and p65 at 0.1 and 0.075 μg respectively repressed the transcriptional activity of GR approximately 500-fold.

b) Increase in PML reverses Tax mediated inhibition of nuclear receptors

CV-1 cells were transfected with expression plasmids expressing GR, Tax, PML and the MMTV-Luc reporter gene in various combinations as described previously. Transient expression of GR (0.05 μg) and reporter induced MMTV-Luc transcription approximately 300-fold in the presence of 1 μM dexamethasone. In cells transiently transfected with GR, MMTV-Luc and Tax (0.18 μg), Tax repressed GR activity by more than 50%. However, in cells transiently transfected with GR, MMTV-Luc and PML (0.10 μg), GR activity was stimulated 5–15 fold. Co-expression of TaxI and PML in increasing molar ration blocked the Tax repression effect on GR and GR regained more than a 300-fold activation on the MMTV reporter plasmid.

Example 7
PODs are and Important Site of Nuclear Receptor and CBP Activity

The following example demonstrates that the transcription factor CBP is a POD-localized protein and that localization to and the integrity of PODs is essential for nuclear receptor function.

a) CBP and PML co-localize to nuclear PODs

To investigate whether CBP localizes to PODs, a double immunofluorescence experiment was undertaken in asynchronous CV-1 cells measuring endogenous proteins. CV-1 cells were maintained as monolayers in Dulbecco's modified Eagle's minimal essential medium (DMEM) supplemented with 10% bovine calf serum (Gibco) and 100 U/ml penicillin-streptomycin. Cultures were maintained at 37 degrees C and in 7% $CO_2$. For immunofluorescence, cells were grown on round coverslips to 80–90% confluency (Corning Glass Inc.) in 6 well plates. The cells were fixed as previously described (Doucas and Evans, Genes & Dev 10:196–207, 1996). The fixed cells were incubated with affinity purified polyclonal rabbit antiserum against human PML (Ab PML 5311, Mab 5E10, PML mouse Ab (Santa Cruz Biotechnology) (Doucas, supra)), or CBP (CBP A22, CBP C20 (Santa Cruz Biotechnology)) diluted in PBS for 1 hour at room temperature. Second antibodies conjugated to fluorescein or Texas red were applied for 1 hour at room temperature in a humidified chamber. Cells were then stained for DNA with 0.5 μg/ml bis-benzimide (Hoechst 33258, Sigma) in PBS and mounted with gelvatol or Fluoromount G (Fisher Scientific). Fluorescence images were analyzed with a Nikon Microsphot-SA immunofluorescence microscope and with confocal microscopy.

PML localization was almost identical with the CBP localization, both of which appeared in a nuclear speckled pattern.

b) PML and CBP interact directly

Given that CBP and PML proteins co-localize in the nucleus, the inventors investigated whether CBP and PML interact at the protein level. CV-1 cells were grown to 50–80% confluency as described above. The cells were transiently transfected with 1–3 μg of expression vectors expressing PML (wild type—CMX-PML, coiled-coil domain deleted—PML (216–331), (217–331)) and CBP (CMX-Gal-CBP.wt) (Doucas, et al, Proc Natl Acad Sci USA 90:9345–9349 (1993). Co-transfection of the wide-type PML increases transactivation by Gal-CBP.wt by 10–12-fold, whereas co-transfection with one of the deletion mutants not only abolished transactivation but repressed the basal level of activity 2–3-fold.

These data indicate that PML is a novel co-factor for nuclear receptor and CBP activity.

c) PML functions as a nuclear receptor co-factor

CV-1 cells, grown as described above, were transiently transfected with 1.2 μg reporter construct (MMTV-Luc), 0.9 μg of CMX-beta-gal, 0.6 μg RSV-GR and expression plasmids containing PML (wild-type or deletion mutants) as previously described. Luciferase and beta-galatosidase were assayed as described in Hollenberg and Evans, Cell 55:899–906, 1988 using 10-fold serial dilutions of dexamethasone from $10^9$ M to $10^{-6}$ M. Extracts were prepared 24–30 hours after transfection. Transient transfection of GR induces MMTV-Luc transcription from 30 to 200 fold in a dexamethasone dependent manner. PML synergizes with GR and activates MMTV transcription 600-fold at 10 mM of dexamethasone.

In a similar experiment, CV-1 cells, grown as described above, were transiently transfected with 1.2 μg reporter construct (Apo14-tk-Luc), 0.9 μg of CMX-beta-gal, 1.2 μg CMX-RXRalpha and the expression vectors containing CBP, PML (wild-type and deletion mutants) as previously described. Apo-tk-Luc contains 4 synthetic oligonucleotides linked to the minimal thymidine kinase promoter upstream of the coding sequence for the luciferase gene. The oligonucleotides correspond to the A site of the apolipoprotein AI promoter (Rottman, et al, Mol Cell Biol. 11:3814–3820, 1991). Transfected cells were treated with 9cis retinoic-acid at 1 μM for 8 hours before the assay. Co-transfection of PML and RXR-alpha enhanced reporter gene transcription 250-fold over cells mock transfected with empty expression vector (CMX). Transfection with PML enhance reported gene activity by 50-fold.

In a third experiment, CV-1 cells were transfected with Gal-RXR alpha F (a Gal-4 DNA binding domain/RXR fusion), CMX-PML, PSVP-PML delta 216–331, and CMX-CBP.m (each 1.2 μg) and treated with 1 μM 9cis retinoic-acid for 8 hours before performing the reporter assay. (These expression plasmids are described in Doucas, et al, Proc Natl Acad Sci USA 90:9245–9349, 1993).) Co-transfection of CBP, PML or the combination augments ligand dependent transcription of the Gal reporter. PML augmented ligand dependent transcription driven by the Gal-4/RXR fusion protein more than 40-fold in a concentration dependent manner. In contrast, expression of the PML deletion mutant failed to enhance transcription and actually acted as a modest transcription inhibitor.

PML expression markedly enhances transcription by RXR and GR reporter genes. PML transactivation on MMTV was most effective at low concentrations of dexamethasone ($10^{-8}$ M) enhancing GR activation by more than 10-fold. In addition, in CV-1 cells, PML potentiates Apo14-tk-Luc transcription by both the endogenous and co-transfected RXR proteins. Finally, in a co-transfection experiment, the PML delta 231–331 mutant did not activate nuclear receptor hormone dependent transcription, as exemplified with both the GR wild-type and fusion Gal-4-RXRalpha F. The strong transcriptional potentiation of PML compared to CBP on transfected RXR and GR and its unique ability to transactivate endogenous nuclear receptors further suggests that PML functions as an essential nuclear receptor and CBP co-factor and that POD structure and function is key to maintaining normal cellular activity.

d) Nuclear receptors are recruited to PODs

CV-1 cells were co-transfected at 70% confluency with CMX-PML and RSV-GR expression vectors (1 and 3 μg, respectively) as previously described. Cells were grown in the absence of dexamethasone or treated with 1 μM dexamethasone for ≦2 min and fixed 12 hours post-transfection. Localization of PML and GR was visualized using anti-PML antibodies or anti-GR antibody (GR 135) as described above. In the absence of ligand, GR is located primarily in the cytoplasm and PML in the nucleus. Treatment with ligand, however, promotes the nuclear translocation of GR into a network-like pattern overlapping with PML. The same results were obtained in a similar experiment employing the co-transfection of CMX-PML and CMX-RXRα.

Example 8
Assay for Substances that Increase Nuclear Receptor Activity

The following example describes assays for identifying potential therapeutic substances by measuring the ability of the substance to enhance nuclear receptor-related transcriptional activity, particularly in the presence of inhibitors of such activity such as Tax or NF-κB.

CV-1 cells, grown as described above, are co-transfected with expression plasmids containing a nuclear receptor gene (such as GR), a reporter gene (such as MMTV-Luc) and a repressor of nuclear receptor activity (such as Tax and/or NF-κB). The transiently transfected cells are treated with a test substance, diluted as described in Examples 1 and 2 above, for approximately 4–16 hours The cells are subsequently treated with a stimulator of nuclear receptor activity (such as dexamethasone) and the amount of nuclear receptor activity measured as a function of the activity of the reporter gene. Substances that enhance nuclear receptor activity, as compared to cells that have not been treated with a test substance, are potential therapeutic agents.

Example 9
Assays for Substances that Modulate POD Structure and/or Function Via Nuclear Receptor Activity The assays methods described above that are utilized in defining substances that modify nuclear receptor-related transcriptional activity can additionally be used to identify substances useful for the modulation of POD structure and/or function.

Tells cells, such as CV1 or Hep-2, are grown as described previously in the presence or absence of a test substance. The techniques described above, such as detection with specific antibodies, can be used to determine if the POD structure and/or function has been disrupted in cells exposed to the test substance as compared to control cells that have not been so exposed.

While the foregoing has been with reference to particular embodiments of the invention, it will be appreciated by those skilled in the art that changes in these embodiments may be made without departing from the principles and spirit of the invention, the scope of which is defined by the appended claims.

What is claimed:

1. An assay method for identifying a substance useful for modulating POD structure or function in a test cell, said method comprising:
   a) contacting a test cell with a test substance,
      wherein the test substance is a protein, peptide, small organic molecule, carbohydrate, lipid, fungal extract, or plant extract,
      wherein said test cell expresses one or more retroviral proteins, including at least Tax, in an amount sufficient to upregulate a promoter of a gene encoding a POD-localized protein, and
      wherein the POD-localized protein is PML, Sp-100, CBP, PIF13, PIF31, ND52, ND55, or DipA, and
   b) assaying for the ability of the test substance to modulate POD function and/or structure in the test cell.

2. The method of claim 1 wherein the test substance upregulates expression of mRNA encoding a POD-localized protein or expression of a POD-localized protein.

3. The method of claim 1 wherein the retroviral proteins are derived from human immunodeficiency virus or a human T lymphotropic virus.

4. An assay method for identifying a substance useful for modulating POD structure or function in a test cell, said method comprising:
   a) contacting a test cell with a test substance, wherein said test cell expresses one or more retroviral proteins, including at least Tax, and a reporter gene whose expression is modulated by a nuclear receptor expressed by the test cell and
   b) assaying for the ability of the test substance to modulate POD function and/or structure in the test cell.

5. The method of claim 4 wherein the viral protein or proteins cause disruption or degradation of POD punctate structure.

6. The method of claim further comprising the step of causing the test cell to express a nuclear receptor and a reporter gene.

7. The method of claim 4 wherein the viral protein or proteins block nuclear receptor mediated transcription.

8. The method of claim 7 further comprising the step of assaying for the ability of the substance to inhibit NF-kappaB, and/or AP-1 transcriptional activity.

9. The method of claim 4 wherein the nuclear receptor is the glucocorticoid receptor, retinoic acid receptor, androgen receptor, estrogen receptor, mineralocorticoid receptor progesterone receptor, or peroxisome proliferator activated receptor.

10. The method of claim 4 wherein the test cell is infected with a virus so as to express said one or more viral proteins.

11. The method of claim 10 wherein the viral proteins are Tax, E4 ORF3, and/or E4 ORF6.

12. The method of claim 10 wherein the virus is a hepatitis virus, herpes virus, human T lymphotropic virus, human immunodeficiency virus, varicella virus, papilloma virus, lentivirus, or adenovirus.

13. The method of claim 12 wherein the viral proteins are derived from hepatitis virus, herpes virus, human T lymphotropic virus, human immunodeficiency virus, varicella virus, papilloma virus, lentivirus, or adenovirus.

14. The method of claim 4 wherein the test cell is genetically engineered so as to express said one or more viral proteins.

15. The method of claim 14 wherein the viral proteins are Tax, E4 ORF3, and/or E4 ORF6.

16. A method of claim 15 wherein the substance is a Tax protein or a Tax protein mimic.

17. A method of claim wherein the substance is a modulator of nuclear receptor transcription.

18. The method of claim 4 wherein the test cells have been genetically engineered to express the nuclear receptor.

19. The method of claim 4 wherein the test substance is a protein, peptide, small organic molecule, carbohydrate, lipid, fungal extract, or plant extract.

20. A method of inhibiting adipocyte differentiation; said method comprising contacting the adipocyte with a substance that disrupts POD function and/or structure.

21. A method of inhibiting adipocyte differentiation; said method comprising contacting the adipocyte with a substance capable of disrupting POD function and/or structure.

22. The method of claim 4 wherein the test cell is infected with a human immunodeficiency virus so as to express said one or more retroviral proteins.

23. The method of claim 4 wherein the retroviral proteins are derived from human immunodeficiency virus.

24. The method of claim 1 wherein the test cell is infected with a human immunodeficiency virus so as to express said one or more retroviral proteins.

25. The method of claim 1 wherein the retoviral proteins are derived from human immunodeficiency virus.

* * * * *